(12) United States Patent
Offenbeck et al.

(10) Patent No.: US 9,810,577 B2
(45) Date of Patent: Nov. 7, 2017

(54) APPARATUS AND METHOD FOR MEASURING A PERIODIC SIGNAL

(71) Applicant: Hamilton Bonaduz AG, Bonaduz (CH)

(72) Inventors: Bernd Offenbeck, Regensburg (DE); Philipp Arquint, Bonaduz (CH)

(73) Assignee: Hamilton Bonaduz AG (CH)

( * ) Notice: Subject to any disclaimer, the term of this patent is extended or adjusted under 35 U.S.C. 154(b) by 221 days.

(21) Appl. No.: 14/654,217

(22) PCT Filed: Oct. 22, 2013

(86) PCT No.: PCT/EP2013/072088
§ 371 (c)(1),
(2) Date: Jun. 19, 2015

(87) PCT Pub. No.: WO2014/095128
PCT Pub. Date: Jun. 26, 2014

(65) Prior Publication Data
US 2015/0300880 A1    Oct. 22, 2015

(30) Foreign Application Priority Data
Dec. 21, 2012   (DE) ......................... 10 2012 113 008

(51) Int. Cl.
*G01J 3/46*     (2006.01)
*G01J 3/28*     (2006.01)
(Continued)

(52) U.S. Cl.
CPC ........ *G01J 3/2803* (2013.01); *A61B 5/14551* (2013.01); *G01J 1/44* (2013.01); *G01J 3/0286* (2013.01); *G01J 3/44* (2013.01)

(58) Field of Classification Search
CPC .......... G01J 3/2803; G01J 1/44; G01J 3/0286; A61B 5/14551
(Continued)

(56) References Cited

U.S. PATENT DOCUMENTS 7,859,673 B2 * 12/2010 Moehler .................. G01J 1/42
250/214 LS 2002/0012152 A1    1/2002 Agazzi et al.
(Continued)

FOREIGN PATENT DOCUMENTS

WO    0178593    10/2001

OTHER PUBLICATIONS

Mark Looney, "Advanced Digital Post-Processing Techniques Enhance Performance in Time-Interleaved ADC Systems," Analog Dialogue 37-8 (Aug. 31, 2003), retrieved from http://www.analog.com/library/analogdialogue/archives/37-08/post_processing.html.

*Primary Examiner* — Hina F Ayub
(74) *Attorney, Agent, or Firm* — Jansson Munger McKinley & Kirby Ltd.

(57) ABSTRACT

A device for measuring a periodic signal includes: a first control unit for generating an electrical input signal (V1) of the period T; a light source for generating an optical input signal directed to an object being measured from the electrical input signal (V1); an optical receiver for detecting and converting the signal reflected from the object being measured, the signal corresponding to the optical input signal altered in terms of phase and amplitude, into an electrical measurement signal (V2); and a plurality of measurement channels connected in parallel between the optical receiver and a second control unit, each measurement channel being connected in series to a switching element, a filter element, and an analog-to-digital converter, wherein the second control unit is suitable for evaluating the measurement signals from the plurality of measurement channels, and in which the electrical measurement signal (V2) is applied to each of the plurality of measurement channels, the first control unit is connected to the plurality of switching elements and is suitable for actuating the switching elements for different time intervals in each case, and the analog-to-digital converters have a maximum sampling rate of less than $2 \times 1/T$.

14 Claims, 4 Drawing Sheets

(51) Int. Cl.
*A61B 5/1455* (2006.01)
*G01J 1/44* (2006.01)
*G01J 3/44* (2006.01)
*G01J 3/02* (2006.01)

(58) Field of Classification Search
USPC .......................................................... 356/402
See application file for complete search history.

(56) References Cited

U.S. PATENT DOCUMENTS

| | | | |
|---|---|---|---|
| 2004/0022161 A1* | 2/2004 | Wood .................... | G03H 1/0244 |
| | | | 369/101 |
| 2004/0061048 A1 | 4/2004 | Vasic et al. | |
| 2006/0030763 A1 | 2/2006 | Mannheimer et al. | |
| 2007/0043269 A1* | 2/2007 | Mannheimer ...... | A61B 5/14551 |
| | | | 600/323 |
| 2007/0132618 A1* | 6/2007 | Petersen ............ | A61B 5/14551 |
| | | | 341/143 |
| 2008/0129369 A1* | 6/2008 | Ivancevic ............ | H03K 17/005 |
| | | | 327/410 |
| 2009/0291658 A1* | 11/2009 | Castle .................. | H04B 1/1638 |
| | | | 455/255 |
| 2009/0315594 A1* | 12/2009 | Pentakota ............... | H03F 3/505 |
| | | | 327/109 |
| 2011/0077485 A1* | 3/2011 | Baker, Jr. ............. | A61B 5/0059 |
| | | | 600/324 |
| 2012/0268299 A1* | 10/2012 | Kidambi ............. | H03M 1/1052 |
| | | | 341/155 |
| 2014/0070971 A1* | 3/2014 | Zabroda ............... | G11C 27/026 |
| | | | 341/122 |

* cited by examiner

APPARATUS AND METHOD FOR MEASURING A PERIODIC SIGNAL

RELATED APPLICATIONS

This application is a U.S. national stage entry from PCT/EP2013/072088 filed Oct. 22, 2013, which claims the benefit of German Patent Application No. 10 2012 113 008.6 filed Dec. 21, 2012, the contents of both applications being incorporated herein by reference in their entirety.

FIELD OF THE INVENTION

The present invention relates to the field of process measurement technology and analysis and in particular to the field of devices and methods for measuring of periodic signals.

BACKGROUND OF THE INVENTION

In sensors of process measurement technology and analysis, optical measuring methods are being used more and more frequently. In these methods, the amplitude and/or phasing of an optical signal changes when it strikes a measurement object, and the changed signal is detected by an optical sensor. An example of the application of an optical measuring method of this type is the measurement of the oxygen content or oxygen saturation of a liquid or a substance, wherein a dye is illuminated by a light signal of a previously determined wavelength, amplitude, and phasing, and the luminescent light reflected from the dye is analyzed. When the oxygen concentration in the dye changes, the fade time of the luminescence and thus the amplitude and phasing of the received optical signal also change. With appropriate calibration, the amplitude and phase of the received optical signal are therefore a measure of the oxygen concentration.

There are essentially two prior-art methods being used today to acquire optical signals in the sensors of processing measurement technology and analysis.

In the first method of the prior art, the device and signal curve of which are shown schematically in FIGS. 1a and 1b, an electrical signal is first generated under the command of a control unit 2 by means of a digital-to-analog converter (DAC) 4 and converted by an LED 6 into an optical signal V1. The optical signal reflected by a dye 8 is converted into an electrical measurement signal V2 in a photodiode 10, detected in its entirety by an analog-to-digital converter (ADC) 12, and finally processed digitally and evaluated in the control unit 2. So that the electrical measurement signal V2 can be acquired as accurately as possible in the ADC, it is necessary for the converter to operate with a high degree of oversampling. The sampling points are represented schematically in FIG. 2 as small, filled circles. For example, in the case of a signal with a frequency of 8 kHz, it is necessary to sample typically at 80-800 kSPS. Such analog-to-digital converters with high oversampling comprise a complex digital logic circuit, and for this reason they consume a relatively large amount of power. In addition, these high oversampling rates produce a large amount of digital data, which must be subjected to further processing by a powerful processor.

In the second known measurement method, for which a sensor is illustrated schematically by way of example in FIG. 2, an electrical measurement signal is generated in a signal generator 11 and converted by an LED 6 into an optical signal V1 as in the case of the first known method. The optical signal V1 is directed at a dye 8; the optical measurement signal reflected by the dye is converted in the photodiode 10 into the electrical measurement signal V2, and this is processed by an analog lock-in amplifier. The lock-in amplifier comprises a phase shifter 14 and two analog mixers or multipliers 16. The low-frequency components of the measurement signal filtered by a low-pass filter 18 are acquired by an analog-to-digital converter (ADC) 12 and evaluated in a control unit 2.

The disadvantage of this second method is that the properties of the analog mixer are strongly influenced by component drift. Such component drift is, however, not acceptable in the case of sensors with built-in circuitry which are used in an expanded temperature range in process measurement technology and which must operate for prolonged periods of time without recalibration. In particular, the use of these types of sensors in zones at high risk of explosion is not possible because of the high power consumption.

U.S. Pat. No. 8,078,246 discloses a sensor for pulsoximetry, in which the electrical measurement signal converted by a photodiode is sent to an input amplifier and then distributed over N measurement channels, each of which processes different wavelengths of the amplified measurement signal. Each measurement channel comprises an analog switch, a low-pass filter, and an analog-to-digital converter, and the output signals of the N measurement channels are evaluated in a control unit. The problem here is the same as that cited in relation to the first known method, namely, that the evaluation of the signal in an individual measurement channel is accurate only when the analog-to-digital converter has sufficiently high resolution and thus a correspondingly high oversampling. The difficulties mentioned above are therefore also encountered with U.S. Pat. No. 8,078,246.

It is therefore the object of the present invention to provide a device and a method for measuring a periodic signal which overcome the disadvantages of the prior art, comprise relatively low power consumption and thus low self-heating, contain simple and low-cost components, and guarantee efficient and accurate measurement. This object is achieved by the present claimed invention. Advantageous embodiments are disclosed and claimed herein.

SUMMARY OF THE INVENTION

According to the invention, a device for measuring a periodic signal includes: a first control unit for generating an electrical input signal of the period T; a light source for generating an optical input signal directed to an object being measured from the electrical input signal; an optical receiver for detecting and converting the signal reflected from the object being measured, said signal corresponding to the optical input signal altered, in terms of phase and amplitude, into an electrical measurement signal; and a plurality of measurement channels connected in parallel between the optical receiver and a second control unit, each measurement channel being connected in series to a switching element, a filter element, and an analog-to-digital converter, wherein the second control unit is suitable for evaluating the measurement signals from the plurality of measurement channels; wherein the electrical measurement signal is applied to each of the plurality of measurement channels, the first control unit is connected to the plurality of switching elements and is suitable for actuating the switching elements for different time intervals in each case, and the analog-to-digital converters comprise a maximum sampling rate of less than $2 \times 1/T$.

By "distributing" the electrical measurement signal over the plurality of measurement channels, the various individual measurement signals can be acquired by slow, low-cost analog-to-digital converters with undersampling, that is, converters which scan below the Nyquist-Shannon sampling rate. Simultaneously, the measurement signals acquired during the different time intervals can be combined in the second control unit, and thus the entire measurement signal can be accurately acquired and processed.

In contrast to the devices and methods of the prior art, the power consumption is considerably lower than that of a single or even of several analog-to-digital converters with oversampling, and it is also lower because the switching elements consume very little power. Because of the lower power consumption, the self-heating of the entire measurement device is decreased, and thus the components can be integrated with greater density. In addition, there is no warmup drift to be expected as a result of self-heating, which means that the device is ready to use immediately. The low power consumption, furthermore, also facilitates the use of the device in environments at risk of explosion.

It is especially preferable for the electrical input signal to be configured as a square-wave signal. As a result, the received luminescence signal comprises essentially a sawtooth form, which can be processed very easily and accurately by the plurality of measurement channels of the device according to the invention.

It is also advantageous for the filter element to be configured as low-pass filters. Low-pass filters can be built out of passive analog components, for example, which are low in cost and easily available. As a result of the low-pass filtering, the measurement signal is integrated in the associated measurement channel; that is, a process of average-value formation takes place.

The switching elements in each of the plurality of measurement channels are preferably configured as CMOS switches or CMOS changeover switches. CMOS technology switches of this type are reliable, simple in design, and available at low cost and are thus especially well-suited to use in the device according to the invention.

It is also advantageous for the first control unit to be connected to, and synchronized with, the second control unit. Thus the overall process of signal processing can be improved, because in particular the exact times at which the periodic measurement signal is sent out and the times at which the switching elements are switched over can be processed directly.

It is especially preferable for an integrated circuit to comprise the first control unit, the second control unit, and the plurality of analog-to-digital converters of the plurality of measurement channels. An integrated circuit of this type can be, for example, a purpose-built microcontroller. Because the functionality of the individual components is not too complex, a microcontroller of this type can be built relatively easily and made available at acceptable cost.

It is also advantageous for the first control unit to comprise a pulse width modulation (PWM) generator. Thus, by means of a simple digital logic circuit, it is possible both to generate the measurement signal and to actuate the sampling, i.e., switching, elements. In the microcontroller itself, into which the PWM generator can be integrated, there is no need to perform calculations to generate the desired signals. The use of a PWM generator is therefore thrifty in terms of both resources and energy.

Also according to the invention is a method for measuring a periodic signal with the following steps: sending an optical input signal from a light source based on an electrical input signal with the period T to an object being measured; receiving and converting an optical measurement signal corresponding to the optical input signal altered in terms of phase and amplitude into an electrical measurement signal in an optical receiver; and tapping the electrical measurement signal by each of a plurality of parallel-connected measurement channels, each of which is connected in series with a switching element, a low-pass filter, and an analog-to-digital converter; wherein the same frequency of the electrical measurement signal is processed in each of the plurality of measurement channels; wherein the electrical measurement signal is tapped by each of the plurality of measurement channels at periodically recurring time intervals, different in each channel, wherein a first control unit actuates the switching elements in each of the plurality of measurement channels; and wherein the electrical measurement signal of each time interval in each of the plurality of measurements channels is integrated in the low-pass filter, converted in the analog-to-digital converter, and evaluated in a second control unit.

The advantages mentioned above in relation to the above-described device also apply to the method according to the invention. In comparison to the previously-mentioned first prior-art method, it can be seen that, in the method according to the invention, as many measurement channels can be used as there are support points within one period of the transmitted signal according to the first prior-art method. The signal is not acquired at just a single point, however; on the contrary, the same range of the electrical measurement signal is integrated over a large number of periods, and thus a reliable average measurement value is formed.

In spite of the large number of relatively simple and low-cost components, it is possible with the device and method of the invention to eliminate complicated and expensive analog-to-digital converters and especially powerful processors. As a result, cost savings are achieved without the need make any sacrifices with respect to measurement accuracy or reliability.

It is preferable for the time intervals in each of the plurality of measurement channels not to overlap. In particular, it is also advantageous for the time intervals in each of the plurality of measurement channels to be of equal length. This means that, in principle, the processing is identical in each of the measurement channels.

It is especially advantageous for the time intervals in each of the plurality of measurement channels to correspond to the period T of the electrical input signal. Thus, in each measurement channel, exactly the same, recurring time segment is sampled over the entire measurement time, integrated, and subjected to analog-to-digital conversion. By assembling the individual output signals from the plurality of measurements channels in the second control unit, it is therefore easily possible to determine the amplitude and the phasing of the measurement signal.

It is also advantageous for the electrical input signal to be formed as a square-wave signal, and the first control unit is preferably synchronized with the second control unit.

It is especially preferable for the maximum sampling rate in each analog-to-digital converter of the plurality of measurement channels to be $<2\times1/T$. As a result of this low sampling rate, which corresponds to an the undersampling below the maximum sampling rate according to the Nyquist-Shannon sampling theorem the requirements on the analog-to-digital converters are significantly reduced, and their power consumption and correspondingly the self-heating of the component during operation are decreased.

As a result of the device method of this invention, the resources of a corresponding electronic circuit, especially those of a modern microcontroller, can be used more efficiently. Because the energy consumption of analog-to-digital converters (ADCs) usually increases with their resolution, that is, with the maximum sampling rate, the present device offers the advantage that only analog-to-digital converters with a very low energy consumption are required, in spite of which a sufficiently high resolution of the measurement signal is still ensured.

BRIEF DESCRIPTION OF THE DRAWINGS

The present invention is described below on the basis of preferred exemplary embodiments with reference to the drawings, in which:

FIG. 1a is a schematic diagram of the above-described first optical measuring device of the prior art.

FIG. 1b is a plot of the measurement signals of the prior-art optical measuring device of FIG. 1a.

DETAILED DESCRIPTIONS OF PREFERRED EMBODIMENTS

Figure 1:
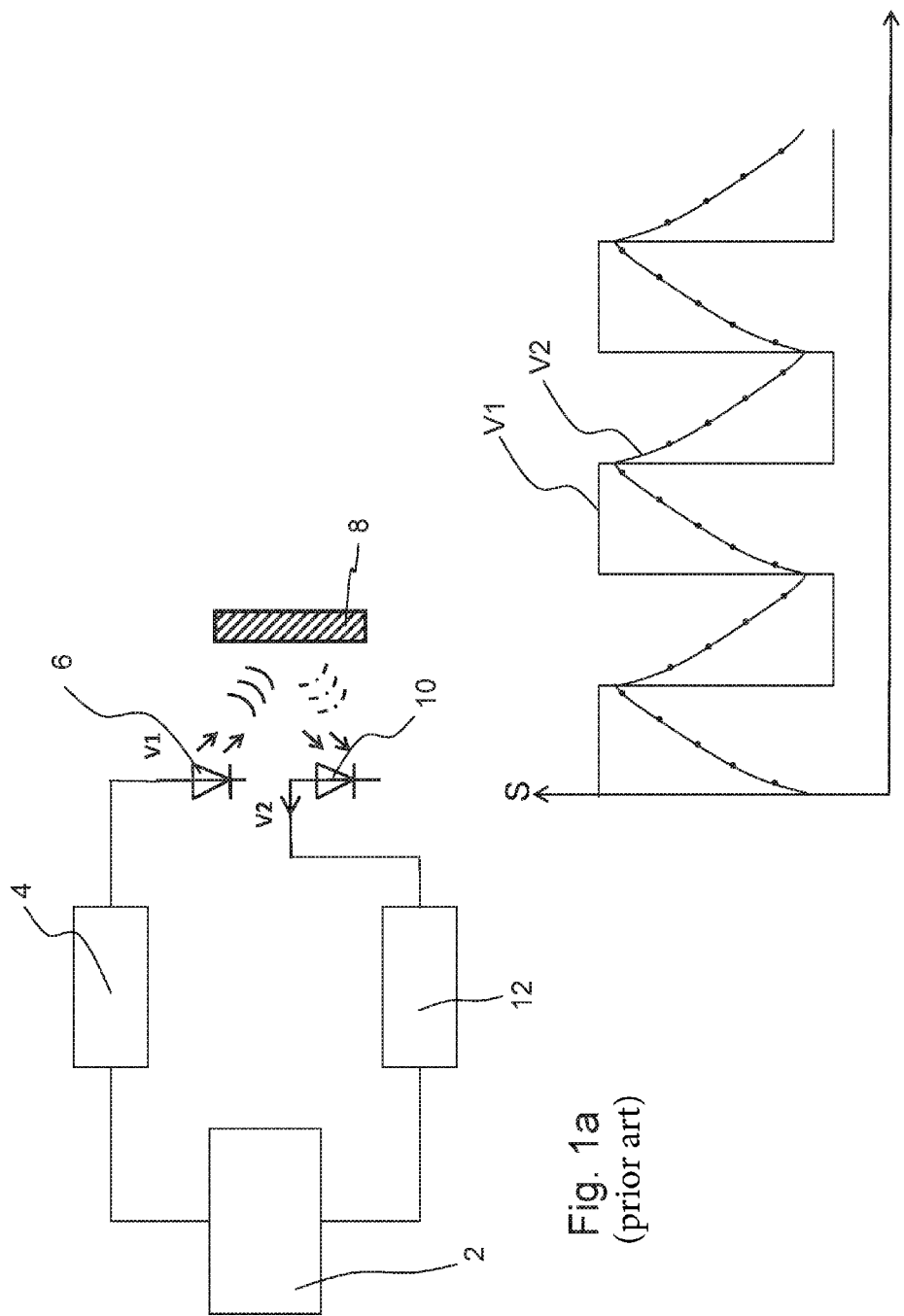
Figure 2:
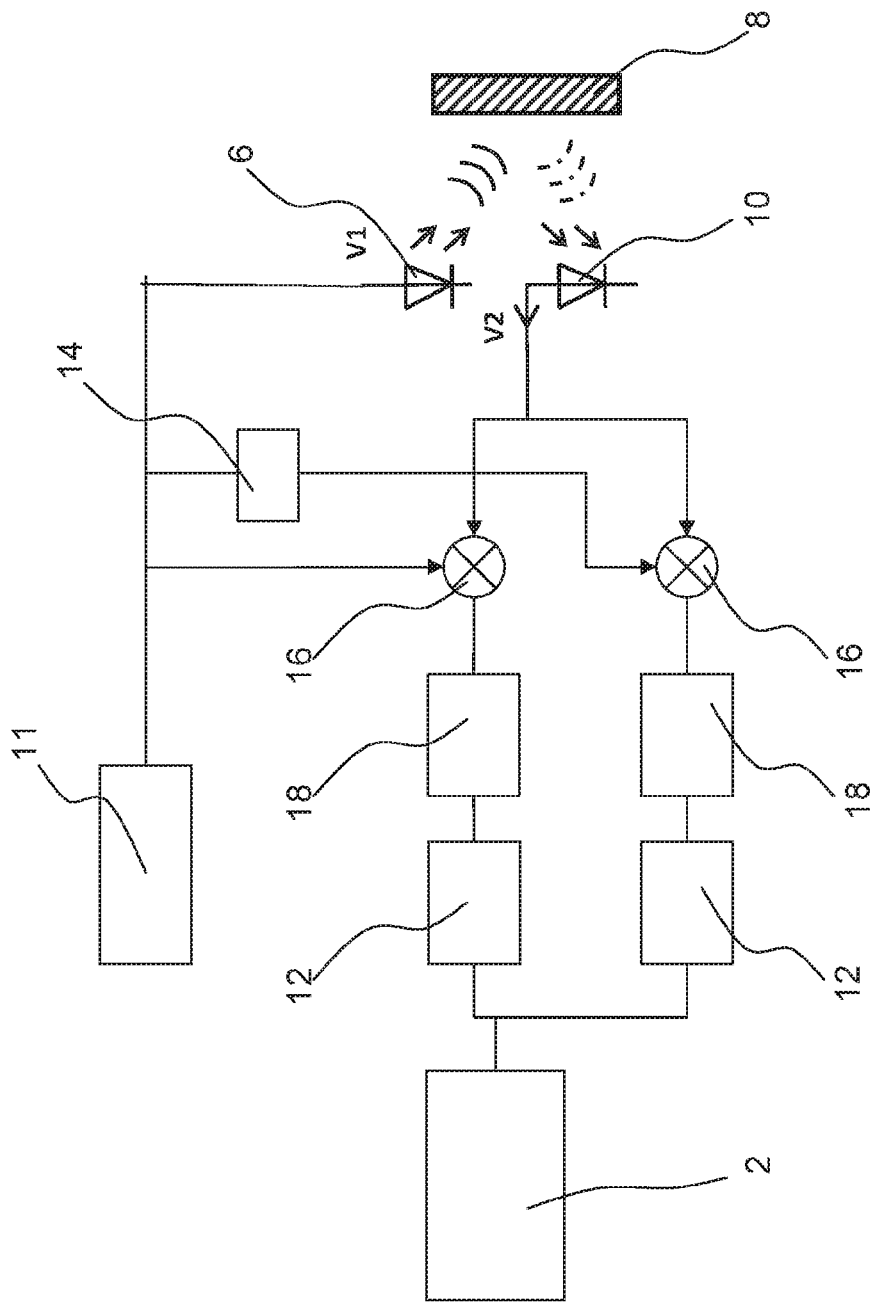
FIG. 2 is a schematic diagram of the above-described second optical measuring device of the prior art.
Figure 3:
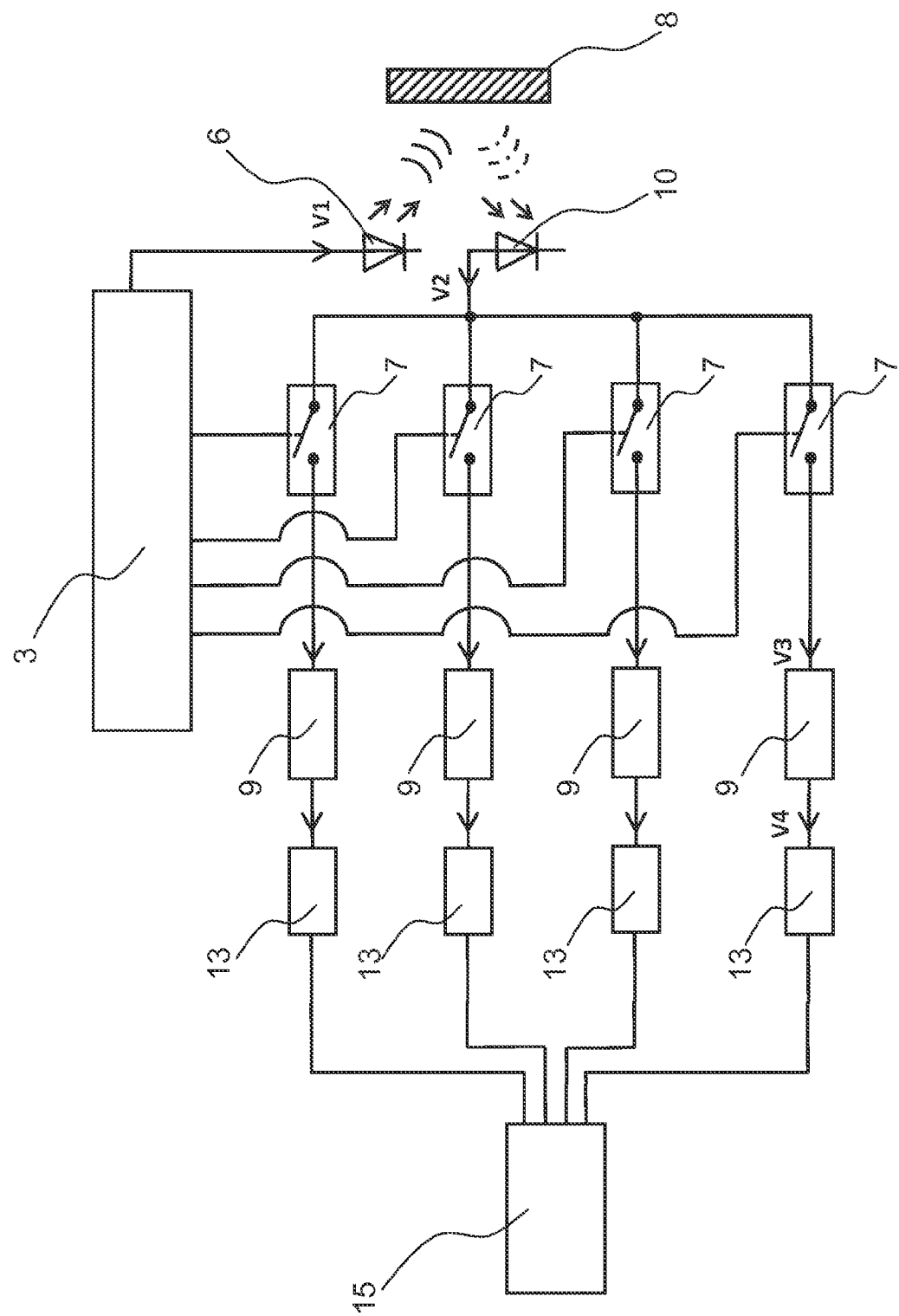
FIG. 3 is a schematic diagram of a preferred embodiment of the invention.

FIG. 3 is a schematic diagram of a preferred device for measuring a periodic signal in accordance with the invention. A first control unit 3 generates a periodic electrical signal V1 with a period T, which is converted in an LED 6 or a similar light source into an optical signal. The optical signal is sent from the LED 6 to a dye 8, wherein, in place of the dye 8 used in the present exemplary embodiment, it is also possible to use some other type of object being measured. The light reflected from the dye 8 is called the "optical measurement signal" and is directed onto a photodiode 10. There it is converted into an electrical measurement signal V2.

The electrical measurement signal V2 is tapped by four measurement channels of essentially identical configuration. Each measurement channel comprises a switching element 7, a low-pass filter 9, and an analog-to-digital converter (ADC) 13, wherein each switching element 7 is connected to the first control unit 3 and the output of each ADC 13 is connected to a second control unit 15. In modifications of the present exemplary embodiment, the number of measurement channels can also be less than or greater than four. The following principle applies: The larger the number of measurement channels, the greater the accuracy of the evaluation of the electrical measurement signal V2.

The switching elements 7 can be configured as analog switches or as CMOS switches, which are actuated, for example, by a PWM generator in the first control unit 3. The electrical measurement signal V2, the period of which corresponds to that of the electrical signal V1, is tapped repeatedly in disjunct time segments of equal length in such a way that the same time segment of each period T is processed by the same measurement channel. A detailed explanation follows below with reference to FIG. 4.

The output signal (designated "V3" in the lowermost measurement channel in FIG. 3) of each switching element 7 represents a periodically recurring segment of the electrical measurement signal V2, wherein the segments in each of the measurement channels do not overlap and, in the preferred embodiment, the sum of the segments from all of the measurement channel delivers the electrical measurement signal V2. This output signal is sent to a low-pass filter 9, which comprises the function of an integrator or arithmetic mean value former and which filters out the low-frequency components of the input signal, i.e., allows the low-frequency components to pass through. Low-pass filters can be configured as passive analog components of simple design, which are sturdy and relatively insensitive to temperature.

The output signal of each low-pass filter, designated "V4" in the lowermost measurement channel in FIG. 3, is sent to an analog-to-digital converter (ADC) 13. There it is processed, i.e., digitized, at a low sampling rate or sampling frequency, which, in the preferred embodiment, is less than 2×1/T. Because the measurement signals in each measurement channel are present only in a small time segment of the overall period T, comparatively slow and low-power-consuming ADCs can be used. This is because, in the time during which no signal is present, there is no need to sample. This considerably reduces the required sampling rate for satisfactory data acquisition, and thus much less expensive and less complex ADCs can be used, which results in a significantly reduced level of power consumption and self-heating.

In the second control unit 15, the output signals of each of ADCs 13 in each of the four measurement channels are evaluated and processed, wherein the differences in phasing and amplitude of the combined measurement signal versus the electrical input signal are a measure of, for example, the oxygen concentration in the dye 8.

Figure 4:
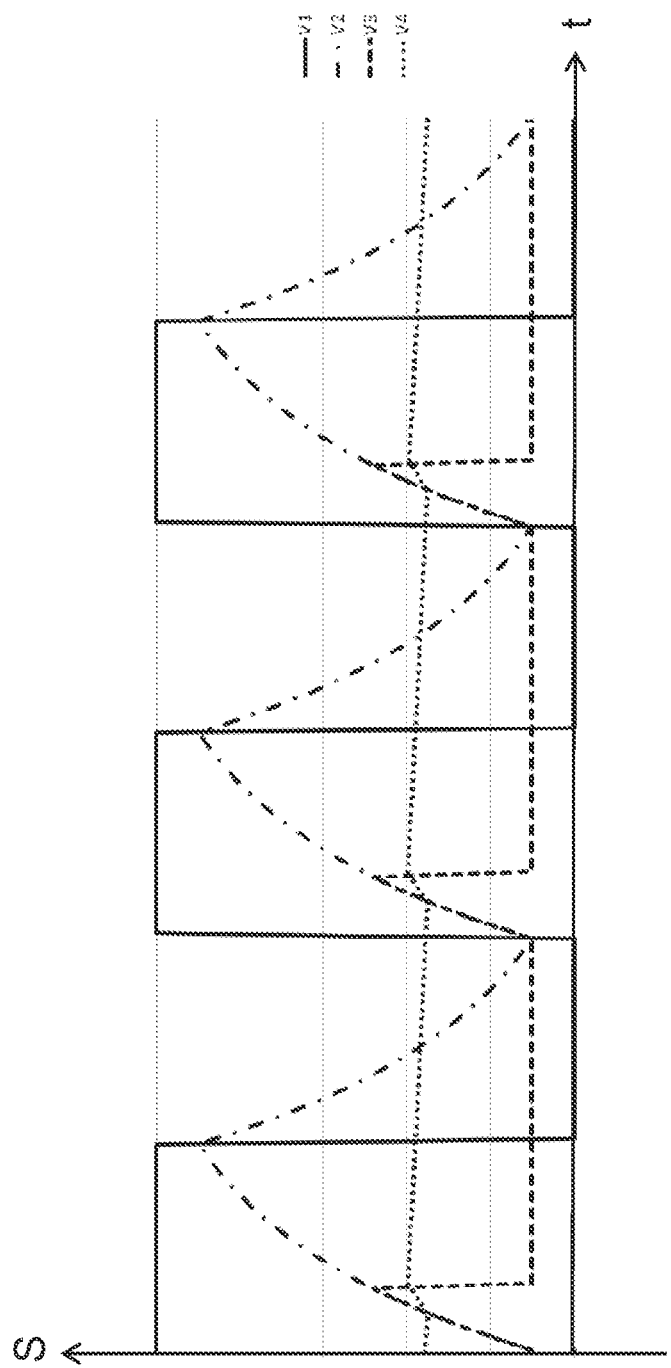
FIG. 4 is a plot of the measurement signals of the device illustrated in FIG. 3.

FIG. 4 shows schematically the course of the electrical input signal V1, the course of the electrical measurement signal V2, and, by way of example for a measurement channel, the course of the output signal V3 of the switching element 7 and of the output signal V4 of the low-pass filter 9. The electrical input signal V1 is a square-wave signal with a period T; the electrical measurement signal or received luminescence signal V2 has a sawtooth form. As a result of the actuation of the switching element 7, the output signal V3 of the switching element 7 describes only a segment of the electrical measurement signal V2, in this case a part of the ascending flank, and the output signal V4 of the low-pass filter represents the integrated measurement signal V3.

With the subject matter of the present invention, a device and a method for measuring a periodic signal are provided, which result in relatively low power consumption and thus low self-heating, which use simple, low-cost components, which ensure efficient and accurate measurement, and which are especially suitable for use in environments at risk of explosion.

The invention claimed is:

1. A device for measuring a periodic signal comprising:
a first control unit for generating an electrical input signal of the period T;
a light source for generating an optical input signal directed to an object being measured from the electrical input signal;
an optical receiver for detecting and converting the signal reflected from the object being measured, said signal corresponding to the optical input signal altered in terms of phase and amplitude, into an electrical measurement signal; and
a plurality of measurement channels connected in parallel between the optical receiver and a second control unit, each measurement channel being connected in series to a switching element, a filter element, and an analogto-digital converter, the second control unit being suitable for evaluating the measurement signals from the plurality of measurement channels;

wherein the electrical measurement signal is applied to each of the plurality of measurement channels, the same frequency of the electrical measurement signal being processed in each of the plurality of measurement channels;

the first control unit is connected to the plurality of switching elements and is suitable for actuating the switching elements for different time intervals in each case; and the analog-to-digital converters comprise a maximum sampling rate of less than $2 \times 1/T$.

2. The device of claim 1 wherein the electrical input signal is configured as a square-wave signal.

3. The device of claim 1 wherein the filter element is a low-pass filter.

4. The device of claim 1 wherein the switching elements in each of the plurality of measurement channels are configured as CMOS switches or CMOS changeover switches.

5. The device of claim 1 wherein the first control unit is connected to and synchronized with the second control unit.

6. The device of claim 1 wherein an integrated circuit comprises the first control unit, the second control unit, and the plurality of analog-to-digital converters.

7. The device of claim 1 wherein the first control unit comprises a pulse width modulation (PWM) generator.

8. A method for measuring a periodic measurement signal, the method comprising the following steps:

sending to an object being measured an optical input signal from a light source based on an electrical input signal with the period T;

receiving and converting an optical measurement signal corresponding to the optical input signal altered in terms of phase and amplitude into an electrical measurement signal in an optical receiver; and tapping the electrical measurement signal by each of a plurality of parallel-connected measurement channels, each of which is connected in series with a switching element, a low-pass filter, and an analog-to-digital converter; and wherein the same frequency of the electrical measurement signal is processed in each of the plurality of measurement channels;

the electrical measurement signal is tapped by each of the plurality of measurement channels at periodically recurring time intervals, different in each channel, wherein a first control unit actuates the switching elements in each of the plurality of measurement channels; and the electrical measurement signal of each time interval in each of the plurality of measurements channels is integrated in the low-pass filter, converted in the analog-to-digital converter, and evaluated in a second control unit.

9. The method of claim 8 wherein the time intervals in each of the plurality of measurement channels are non-overlapping.

10. The method of claim 8 wherein the time intervals in each of the plurality of measurement channels are all of equal length.

11. The method of claim 8 wherein the time intervals in each of the plurality of measurement channels correspond to the period T.

12. The method of claim 8 wherein the electrical input signal is formed as a square-wave signal.

13. The method of claim 8 wherein the first control unit and the second control unit are synchronized with each other.

14. The method of claim 8 wherein in each analog-to-digital converter of the plurality of measurement channels, the maximum sampling rate is less than $2 \times 1/T$.

* * * * *